(12) United States Patent
Berg et al.

(10) Patent No.: US 11,067,588 B2
(45) Date of Patent: Jul. 20, 2021

(54) MEDICAL ANALYTE TESTING SYSTEM AND OPERATING METHOD THEREFOR

(71) Applicant: Roche Diabetes Care, Inc., Indianapolis, IN (US)

(72) Inventors: Max Berg, Mannheim (DE); Hans Kintzig, Tiefenthal (DE); Beate Koschorreck, Schriesheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 184 days.

(21) Appl. No.: 16/183,177

(22) Filed: Nov. 7, 2018

(65) Prior Publication Data

US 2019/0072574 A1 Mar. 7, 2019

Related U.S. Application Data

(63) Continuation of application No. PCT/EP2017/061390, filed on May 11, 2017.

(30) Foreign Application Priority Data

May 11, 2016 (EP) ..................................... 16169232

(51) Int. Cl.
*G01N 35/00* (2006.01)
*G01N 33/487* (2006.01)

(52) U.S. Cl.
CPC . *G01N 35/00663* (2013.01); *G01N 33/48785* (2013.01); *G01N 35/00009* (2013.01);
(Continued)

(58) Field of Classification Search
None
See application file for complete search history.

(56) References Cited

U.S. PATENT DOCUMENTS

| 5,510,082 A | 4/1996 | Arai et al. |
| 8,301,395 B2 | 10/2012 | Matievich, Jr. et al. |

(Continued)

FOREIGN PATENT DOCUMENTS

| CN | 102016574 A | 4/2011 |
| CN | 102308278 A | 1/2012 |

(Continued)

OTHER PUBLICATIONS

Nichols, J.H., Risk management for point-of-care testing, The Journal of the International Federation of Clinical Chemistry and Laboratory Medicine, pp. 154-161 (Year: 2014).*

(Continued)

*Primary Examiner* — Xiaoyun R Xu
(74) *Attorney, Agent, or Firm* — Bose McKinney & Evans LLP

(57) ABSTRACT

A method for operating a medical analyte testing system having a handheld meter, particularly, a glucose meter, and a test magazine is disclosed. In the disclosed method a replaceable test magazine including a plurality of test elements is provided in the handheld meter for conducting successive analyte tests. An auxiliary measuring unit of the handheld meter measures at various points of time at least one ambient parameter, including temperature or humidity. The method checks for a threshold violation by comparing the measured ambient parameter with a preset threshold. The preset threshold is lowered after an initial period of use of the test magazine, and a use-up period is adjusted based on the check for a threshold violation.

19 Claims, 2 Drawing Sheets

(52) U.S. Cl.
CPC .............. *G01N 2035/00019* (2013.01); *G01N 2035/00673* (2013.01)

(56) References Cited

U.S. PATENT DOCUMENTS

| | | |
|---|---|---|
| 2009/0182244 A1 | 7/2009 | Hoenes |
| 2010/0198142 A1 | 8/2010 | Sloan et al. |
| 2011/0077480 A1 | 3/2011 | Bloom et al. |

FOREIGN PATENT DOCUMENTS

| | | |
|---|---|---|
| EP | 1 624 303 A2 | 2/2006 |
| JP | 2010-8100 A | 1/2010 |
| JP | 4434357 B2 | 3/2010 |
| KR | 10 2010 0018563 A | 2/2010 |
| KR | 10 2015 0079965 A | 7/2015 |
| WO | WO 2011/122541 A1 | 10/2011 |

OTHER PUBLICATIONS

International Preliminary Report on Patentability and Written Opinion of the International Searching Authority, PCT/EP2017/061390, dated Apr. 25, 2018, 12 pages.

\* cited by examiner

MEDICAL ANALYTE TESTING SYSTEM AND OPERATING METHOD THEREFOR

RELATED APPLICATIONS

This application is a continuation of PCT/EP2017/061390, filed May 11, 2017, which claims priority to EP 16 169 232.2, filed May 11, 2016, both of which are hereby incorporated herein by reference in their entirety.

BACKGROUND

This disclosure concerns a method for operating a medical analyte testing system including a handheld meter and a test magazine, in particular a handheld blood glucose meter and a test tape cassette. This disclosure further concerns a medical analyte testing system having a handheld meter and a test magazine.

In the field of blood glucose testing, it is known to provide such analyte testing systems with a plurality of test elements for multiple successive tests. Specifically, test elements can be provided as chemistry fields on a test tape, which is loadable into the meter in the form of a replaceable tape cassette. The user then does not need to take care of disposal of each single test element. However, the test chemistry is susceptible to environmental influences, such as humidity and temperature. While the stock keeping is possible in a covering packaging, the disposables are less protected when exchanged into the meter and exposed to ambient air. In order to guarantee reliable measurements, the usual approach is to assume the worst case of environmental stress for determining a fixed use-up period.

SUMMARY

This disclosure provides an improved system and operating method and defines an optimized use term while ensuring reliable tests.

This disclosure is based on the idea of variably setting a permissible exposure period to environmental stress. Thus, a method for operating a medical analyte testing system is proposed according to this disclosure which comprises the steps of:
providing a replaceable test magazine including a plurality of test elements in the handheld meter for conducting successive analyte tests,
measuring at least one ambient parameter including at least one of temperature and humidity by means of an auxiliary measuring unit of the handheld meter at various points in time,
checking for a threshold violation by comparing the at least one measured ambient parameter with a preset threshold, and
adjusting a use-up period (i.e., the period of time within which the test magazine can or should be operable) of the test magazine based on the check in the checking step.

Depending on the influence of the measured parameter, a threshold violation may be defined as exceeding or falling below a preset threshold value. Ambient parameters may also include other variables besides air temperature and humidity, for example exposure to electromagnetic irradiation. In contrast to a laboratory analyzer, a handheld meter in a self-care regimen may be unpredictably used in very different environments. In accordance with this disclosure, it is possible to take into account an individual stress history for determining a significantly prolonged use-up period under uncritical conditions. Furthermore, it is possible to detect critical interferences and to prevent use of unreliable test elements.

Advantageously, the use-up period is adjusted depending on a number and/or a magnitude of one or more threshold violations.

Preferably, the use-up period is extended when a threshold violation is not observed, thus achieving an improved convenience for the user.

Another improvement in this direction provides that the use-up period is defined to comprise a fixed initial period after first use of the test magazine and a variable extension period following the initial period, wherein only the extension period is adjusted. In this way, the user must not accept a disadvantage as compared to conventional systems with fixed use-up term.

In order to avoid inaccurate test results, it is advantageous when the use-up period is set to end in case of a single threshold violation of a predefined critical magnitude.

It is also preferred that the use-up period is set to end when a cumulative number of threshold violations exceeds a predefined maximum number, i.e., a predefined integer value. This allows in an easy way to account for a summary stress inspection.

For further safety improvement it is advantageous when the handheld meter is configured to allow, during the use-up period, use of the test magazine for conducting analyte tests in an analyte measuring unit of the handheld meter, and otherwise to prevent use.

Another improvement in this regard provides that further use of the test magazine is prevented after a fixed expiry date assigned to the test magazine.

A particular embodiment further comprises that the preset threshold is lowered at least at a point in time following a threshold violation. Thus, an interfering influence on the next test can be strictly monitored. This is particularly important when test elements are transported successively to an exposed application site of the meter.

For a clear differentiation between initial and extended use, it is particularly advantageous when the preset threshold is lowered during the use-up period after an initial period of use of the test magazine. Thus, the use in a following extended period of use is allowed under tightened conditions, whereas inconvenience for the user in the initial use period is avoided. Specifically, for the extended period of use, such measures account for a possible lowering of the analyte measuring capability of the test chemistry provided on test elements of the test tape.

Another improvement in this direction comprises shortening, after an initial period of use of the test magazine, a period of time between subsequent measurements of the at least one ambient parameter.

Usually, the stress checking is conducted in connection with an activation of the meter for conducting an analyte test. According to a very preferred embodiment, the auxiliary measuring unit is activated automatically and independently of an analyte measuring at points in time preferably by a timer, and the at least one ambient parameter is measured independently of conducting an analyte test. In this way, a stricter tracking of stress parameters can be achieved, while avoiding unnecessary test consumption.

For measuring of the at least one ambient parameter, if at the relevant point in time the handheld meter is not in an active state, it is also advantageous to turn on the meter automatically without user intervention. In order to reduce energy consumption, it is also conceivable powering only selected components including the auxiliary measuring unit during the automated "awakening" of the meter.

According to a preferred implementation, one or more use parameters of the test magazine comprising at least one of first date of use, expiry date, current (actual) threshold violation and cumulative number of threshold violations may be stored on a storage means assigned or affixed to the test magazine. Thereby, it is also possible to interchangeably use different magazines in different devices.

In is further advantageous when the user is informed about a threshold violation, e.g., on a display of the meter.

Another aspect of this disclosure concerns a medical analyte testing system including a handheld meter and a test magazine, in particular a handheld blood glucose meter and a test tape cassette, wherein the handheld meter comprises an analyte measuring unit for conducting successive analyte tests on test elements provided in the test magazine, wherein the handheld meter comprises an auxiliary measuring unit configured for cyclical measuring at least one ambient parameter including at least one of temperature and humidity, and further comprises a processor operable for checking a threshold violation by comparing the measured ambient parameter with a preset threshold and for adjusting a use-up period of the test magazine based on the checking of a threshold violation.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
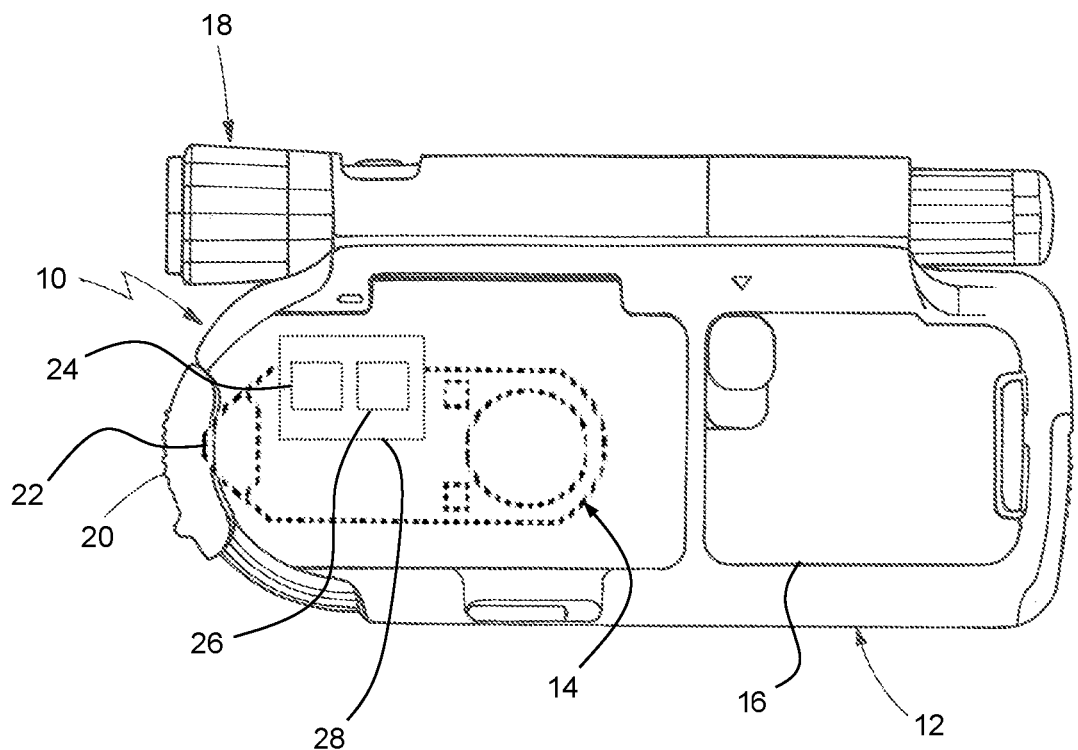
FIG. 1 is a bottom view of a handheld blood glucose meter configured for using a test tape cassette.

In the drawings, an exemplary embodiment of a medical analyte testing system for testing an analyte in a body fluid, specifically glucose in a blood sample is shown. As depicted in FIG. 1, the system 10 at least comprises a portable blood glucose meter 12 and a disposable test tape cassette 14 which can be inserted into the meter 12. The meter is powered by batteries or accumulators provided in a compartment 16. Optionally, a lancing aid 18 is attached to the meter 12 for simplifying lancing of a body part in order to sample blood.

For carrying out an analyte test, a tip cover 20 of the meter 12 can be opened for application of a sample on an active test element 22 provided on a tip of the cassette 14 by means of a rollable test tape of the cassette 14. Then, an analyte measuring unit 24 allows a measurement of an analyte concentration, e.g., by photometrically scanning the test element 22. The test result can be displayed to the user on a display which is arranged on the top side of the meter 12 (not shown).

The cassette 14 serves as a test magazine, as a plurality of test elements 22 is provided on the test tape for successive use. For measuring an ambient parameter such as temperature and/or humidity, an auxiliary measuring unit 26 is connected to a micro-processor 28 of the meter 12. Thereby, a use-up period of the cassette 14 in use can be variably determined, as explained further below.

Figure 2:
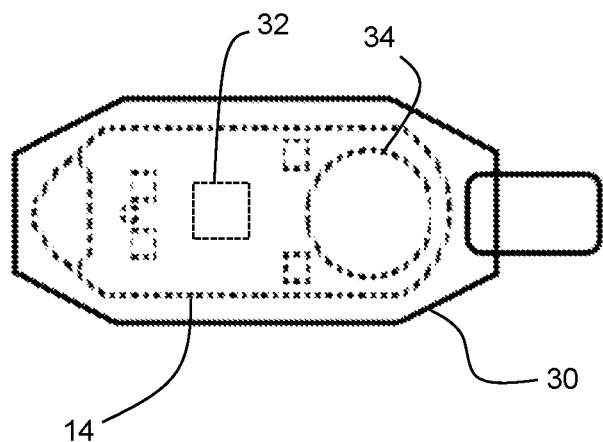
FIG. 2 shows a test tape cassette in an outer packaging.

FIG. 2 shows an unused cassette 14 in an air-tight outer packaging 30. Inside this packaging, the cassette 14 can be further protected against humidity by a desiccant. An RFID-chip 32 is attached on the outer body of the cassette 14 for storing information which can be used in the meter 12. The test tape is provided on a supply spool 34 which is arranged in a sealed storage chamber of the cassette 14. The test elements 22 contain a dry test chemistry wherein enzymes are susceptible to thermal denaturation. Humidity also deteriorates the test chemistry. Therefore, a fixed expiry date is assigned to the packaged cassette 14 and stored in the RFID-chip 32. Furthermore, when the cassette 14 is unpacked and inserted into the meter 12, a use-up period is set for the cassette 14 in order to guarantee the necessary quality of the test chemistry.

Figure 3:
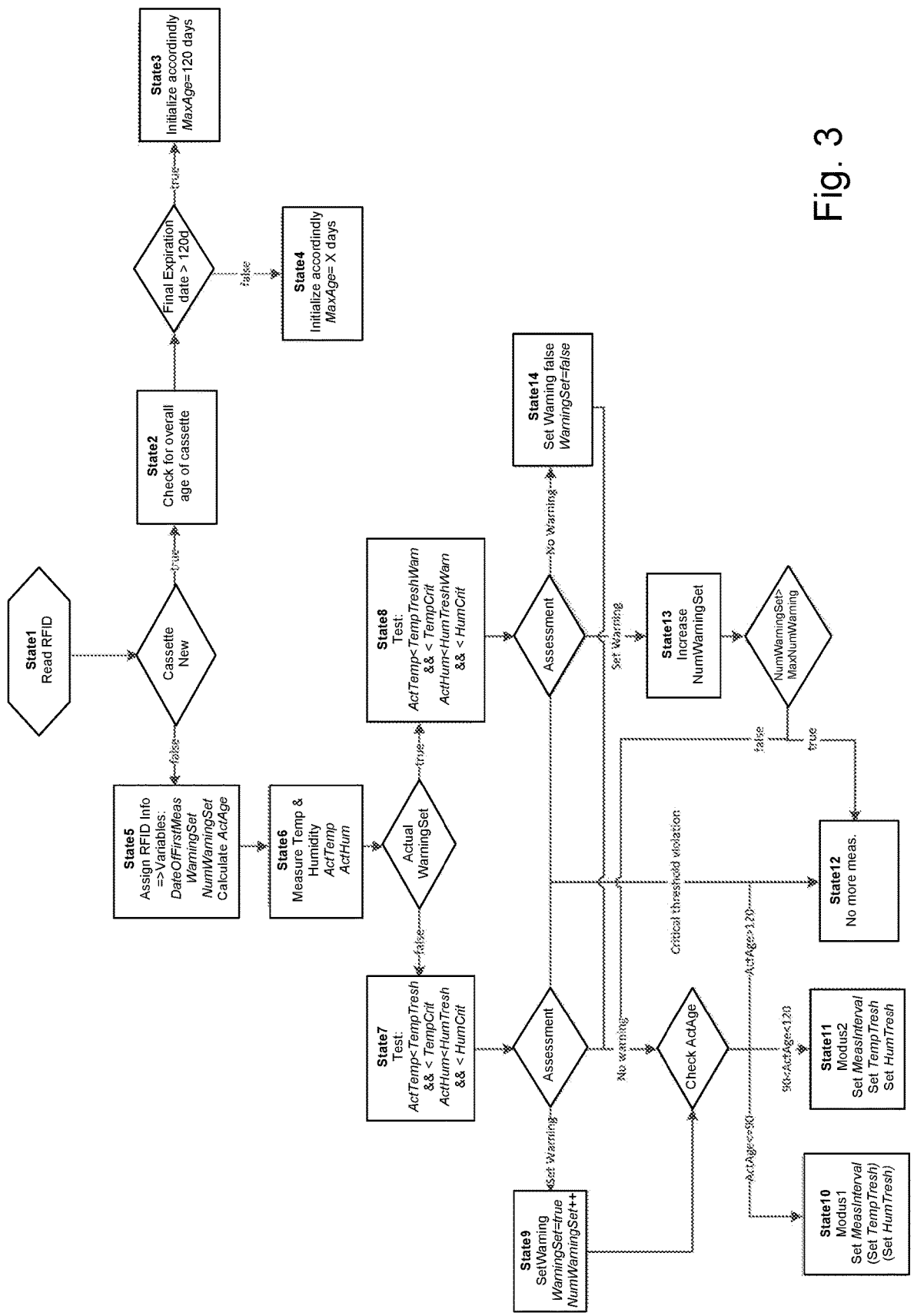
FIG. 3 is a flow-chart of a method for controlling the use-up period of the unpacked test tape cassette in the blood glucose meter.

FIG. 3 illustrates in a flow-chart a method for variably controlling the use-up period. At state 1, the meter 12 reads the RFID-chip 32 in order to check whether the cassette 14 is new or not. If true, at state 2, the overall age of the cassette 14 is determined. The expiry date should not be exceeded. Then, a possible extended use-up period (variable MaxAge) is determined as a maximum of, e.g., 120 days or less, if the time difference between the expiry date and the actual date is less than 120 days. Thereafter, the date of first use/ measurement and the use-up period are written to the RFID-chip 32, and the procedure is terminated.

If the cassette is not new, at state 5, the readout RFID information is assigned to variables, namely the date of first measurement (DateOfFirstMeas), a flag about a past warning (WarningSet) and an integer number (NumWarningSet) for adding up the occurrence of warnings.

As the cassette already has a history, the "stress" due to environmental conditions is checked. At state 6, the actual ambient temperature and humidity are measured by means of the auxiliary measuring unit 26, and corresponding variables (ActTemp, ActHum) are set. In case that the actual WarningSet is false, i.e., no warning has been set at the previous measurement, the actual ambient temperature and humidity are compared to preset normal thresholds at state 7. If the measured temperature is below a temperature threshold (TempTresh) and the measured humidity is below a humidity threshold (HumTresh), then no warning is issued. However, if a threshold is violated, the warning flag (WarningSet) is set true, and the number of warning sets (NumWarningSet) is increased by one.

The assessment after state 7 further includes a comparison of the actual ambient temperature and humidity with thresholds of a predefined critical magnitude (TempCrit and HumCrit), which are above the normal thresholds. In the case of a critical threshold violation, the process is terminated at state 12, where no more measurements with the given cassette are allowed.

Following the assessment after state 7 in the event of a warning (state 9) or of no warning, the actual age of the cassette (ActAge) is checked, which results in three possible cases. In the first case, when ActAge is less than a predefined initial period, e.g., 90 days, the procedure ends at state 10, allowing the user to carry out an analyte measurement without restrictions. In this mode, a relatively broad measuring interval (MeasInterval) is set for carrying out the next checking in a future point in time. Such a checking may be independently of conducting an analyte test. For this purpose, the auxiliary measuring unit 26 may be activated by a timer. Furthermore, in order to ensure usability of the cassette in the initial period, the threshold TempTresh and HumTresh may be set close to the upper critical values.

In the second case of the age check, where the cassette reaches the extended use period between 90 and 120 days, the measuring interval for repeating the stress test is shortened. Here, it should be noted that the available battery power of the meter 12 limits the repetition of stress checks. With the transition into the extended use phase in state 11, the thresholds TempTresh and HumTresh are lowered to a stricter limit, such that a sufficient analyte measuring capability of the test elements 22 is ensured.

It goes without saying that in the third case of the age check, if the actual age has passed the maximum age of, e.g., 120 days, the procedure ends in state 12 without allowing further analyte measurements.

An important aspect of the procedure relates to the strengthening of the stress test in case of a previous threshold violation. Considering that the next test element 22 is close to the seal of the supply chamber of the cassette 14 and therefore subject to increased environmental interferences, lower thresholds TempTreshWarn and HumTreshWarn are applied in state 8 after a warning was set (WarningSet=true). In this assessment, leading to state 14 if no threshold violation is observed, the warning for a next measurement is reset (WarningSet=false) and the procedure continues with the previously explained age check. Thus, the stress check is not based on average values of the ambient parameters, which would be meaningless for the test quality when keeping the portable meter 12 in different locations, for example in a hot car and in a fridge.

On the other hand, when the warning threshold is repeatedly violated, i.e., ActTemp≥TempThresWarn and/or ActHum≥HumThresWarn, the cumulative number of warnings NumWarningSet is increased in state 13. Then, if this number exceeds a predefined maximum number, the use-up period is set to end and no more measurements are allowed in state 12. In the other case (NumWarningSet<MaxNumWarning), the procedure continues with the age check, as explained above.

The user may be informed about a threshold violation, e.g., on the display of the meter 12. It is also conceivable that the system 10 may continue to function upon reaching state 12, while the analyte tests will be flagged accordingly.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for operating a medical analyte testing system having a handheld meter and a test magazine, the method comprising:
   (a) providing a replaceable test magazine in the handheld meter, the test magazine including a plurality of test elements for conducting successive analyte tests;
   (b) using an auxiliary measuring unit of the handheld meter to measure at various points of time at least one ambient parameter, including at least one of temperature and humidity;
   (c) checking for a threshold violation by comparing the at least one measured ambient parameter with a preset threshold;
   (d) lowering the preset threshold after an initial period of use of the test magazine; and
   (e) adjusting a use-up period of the test magazine based on the check in step (c).

2. The method of claim 1, wherein the use-up period is adjusted as a function of number and/or a magnitude of one or more threshold violations.

3. The method of claim 1, wherein the use-up period is extended when a threshold violation is not observed.

4. The method of claim 1, wherein the use-up period is set to end upon the occurrence of a single threshold violation of a predefined critical magnitude.

5. The method of claim 1, wherein the use-up period is set to end when a cumulative number of threshold violations exceeds a predefined maximum number.

6. The method of claim 1, further comprising configuring the handheld meter to allow, during the use-up period, use of the test magazine for conducting analyte tests in an analyte measuring unit of the handheld meter.

7. The method of claim 1, wherein use of the test magazine is prevented after a fixed expiration date assigned to the test magazine.

8. The method of claim 1, further comprising lowering the preset threshold following a threshold violation.

9. The method of claim 1, further comprising increasing, after the initial period of use of the test magazine, the frequency of subsequent measurements of the at least one ambient parameter.

10. The method of claim 1, further comprising activating the auxiliary measuring unit for measuring the at least one ambient parameter independently of conducting an analyte test.

11. The method of claim 10, further comprising using a timer for measuring the at least one ambient parameter.

12. The method of claim 1, further comprising storing one or more use parameters of the test magazine, the use parameters including at least one of first date of use, expiration date, current threshold violation and cumulative number of threshold violations recorded in a storage medium assigned or affixed to the test magazine.

13. The method of claim 1, further comprising generating a warning of a threshold violation.

14. The method of claim 1, wherein the analyte is glucose and the handheld meter measures glucose concentration.

15. The method of claim 4, wherein the use-up period is set to end upon the occurrence of any one of:
   i) a single threshold violation of a predefined critical magnitude;
   ii) when a cumulative number of violations of the preset threshold exceeds a predefined maximum number; or
   iii) the use-up period has reached a predefined maximum time period.

16. The method of claim 15, further comprising activating the auxiliary measuring unit for measuring the at least one ambient parameter independently of conducting an analyte test and wherein the frequency of measurements of the at least one ambient parameter is increased after the fixed initial period of use.

17. The method of claim 15, further comprising lowering the preset threshold following a threshold violation.

18. The method of claim 17, wherein the at least one ambient parameter includes both the ambient humidity and the ambient temperature.

19. The method of claim 18, further comprising activating the auxiliary measuring unit for measuring the at least one ambient parameter independently of conducting an analyte test and wherein the frequency of measurements of the at least one ambient parameter is increased after the fixed initial period of use.

* * * * *

UNITED STATES PATENT AND TRADEMARK OFFICE
CERTIFICATE OF CORRECTION

PATENT NO. : 11,067,588 B2  
APPLICATION NO. : 16/183177  
DATED : July 20, 2021  
INVENTOR(S) : Max Berg, Hans Kintzig and Beate Koschorreck Page 1 of 1

It is certified that error appears in the above-identified patent and that said Letters Patent is hereby corrected as shown below:

In the Claims

Column 6, Line 11, Claim 1, the phrase "the check in step (c)" should read --the check in step (c) wherein the use-up period is defined to include a fixed initial period of use after first use of the test magazine and a variable extension period following the fixed initial period of use--.

Column 6, Line 52, Claim 15, the phrase "The method of claim 4" should read --The method of claim 1--.

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*